(12) United States Patent
Oh et al.

(10) Patent No.: US 7,764,368 B2
(45) Date of Patent: Jul. 27, 2010

(54) METHOD AND APPARATUS FOR INSPECTING DEFECTS ON MASK

(75) Inventors: Sung Hyun Oh, Cheongju-si (KR); Yong Kyoo Choi, Cheongju-si (KR); Byung Sup Cho, Cheongju-si (KR)

(73) Assignee: Hynix Semiconductor Inc., Icheon-si (KR)

( * ) Notice: Subject to any disclaimer, the term of this patent is extended or adjusted under 35 U.S.C. 154(b) by 196 days.

(21) Appl. No.: 11/965,197

(22) Filed: Dec. 27, 2007

(65) Prior Publication Data

US 2008/0186497 A1    Aug. 7, 2008

(30) Foreign Application Priority Data

Feb. 2, 2007    (KR) ...................... 10-2007-0011154

(51) Int. Cl.
*G01N 21/00* (2006.01)

(52) U.S. Cl. ............... 356/237.4; 356/237.1; 356/237.5

(58) Field of Classification Search ... 356/237.4–237.5, 356/237.1, 239.1; 250/559.39–559.49, 440.11–442.11, 250/491.1–492.2
See application file for complete search history.

(56) References Cited

U.S. PATENT DOCUMENTS

| | | | | |
|---|---|---|---|---|
| 5,909,030 | A * | 6/1999 | Yoshitake et al. | ........ 250/492.2 |
| 2002/0081501 | A1* | 6/2002 | Hasegawa et al. | ............... 430/5 |
| 2004/0012776 | A1* | 1/2004 | Bae | ........................... 356/237.4 |
| 2004/0146295 | A1 | 7/2004 | Furman et al. | |
| 2005/0009355 | A1 | 1/2005 | Cho et al. | |
| 2005/0111727 | A1* | 5/2005 | Emery | ......................... 382/145 |
| 2005/0282299 | A1 | 12/2005 | Kim et al. | |
| 2006/0158642 | A1 | 7/2006 | Tanaka | .................... 356/237.5 |
| 2008/0237486 | A1* | 10/2008 | Zhang | ...................... 250/491.1 |

FOREIGN PATENT DOCUMENTS

| | | |
|---|---|---|
| CN | 1786698 | 6/2006 |
| JP | 2000-147747 | 5/2000 |
| KR | 10-2004-0038998 | 5/2004 |

* cited by examiner

*Primary Examiner*—Tarifur Chowdhury
*Assistant Examiner*—Michael Lapage
(74) *Attorney, Agent, or Firm*—Marshall, Gerstein & Borun LLP

(57) ABSTRACT

Provided are a method and apparatus for inspecting mask defects. The method may include preparing a mask with a defect inspecting pattern, formed on a transparent substrate. The method may further include preparing a wafer defect inspecting apparatus including a defect inspecting unit capable of detecting defects through radiating light on a surface of a mask and obtaining an image based on reflected light, and a mask stage on which the mask is mounted facing the defect inspecting unit. The mask stage may replace the wafer stage of a wafer defect inspecting apparatus, and the mask stage may support the mask at a surface height substantially equal to a surface height of the wafer mounted on the wafer stage. The method may also include mounting the mask on the mask stage and detecting mask defects through operating the defect inspecting unit to radiate light on a surface of the mask and obtain an image based on reflected light.

17 Claims, 5 Drawing Sheets

METHOD AND APPARATUS FOR INSPECTING DEFECTS ON MASK

CROSS-REFERENCE TO RELATED APPLICATIONS

The present application claims priority to Korean patent application number 10-2007-0011154, filed on Feb. 2, 2007, which is incorporated by reference in its entirety.

FIELD OF INVENTION

This patent relates to lithography technology, and more particularly, to a method and apparatus for inspecting mask defects.

BACKGROUND OF THE INVENTION

Lithography processing is used for forming circuit patterns that form a semiconductor device on a wafer. In lithography processing, a mask with a pattern to be transcribed on a wafer is used. The mask includes a light shielding layer of chrome (Cr) on a substantially transparent mask substrate or a mask layer of a halftone phase shift layer. A resist layer is deposited for patterning the mask layer and electron beam write equipment is used for electron beam exposure, after which developing is performed and a resist pattern is formed. This resist pattern is used as an etching mask to selectively etch the mask layer in order to form a mask pattern. In order to check if the mask pattern has been formed accurately and according to specifications, a mask defect inspection is performed.

A mask defect inspection involves obtaining an image based on light from a backlight that is transmitted through the mask. Due to increasing reductions of design rules for semiconductor devices, the sizes of defects (which affect yield) are also decreasing. However, existing mask defect inspecting apparatuses are insufficiently capable of detecting smaller defects.

Masks have pellicles attached in order to protect the mask patterns from external impurities. Thus, in the inspection of mask defects, when taking the pellicles into consideration, a working distance (that is the actual distance between an immersion lens unit of a defect detector and the surface of a mask) is set. Keeping in mind the mounting of the pellicle, the inspection gap is set at approximately 6.3 mm. Thus, because the inspection gap is set at a substantial width, it is difficult to realize an immersion lens with a high number of apertures (NA). Because a high NA is difficult to realize, the resolution of an obtained image is relatively low, limiting detection of defects.

Accordingly, there is a need to develop a defect inspecting method with higher resolution that can detect defects of a smaller size that accompany finer mask patterns.

SUMMARY OF THE INVENTION

Various embodiments of the present invention relate to a method for inspecting mask defects, which may include: preparing a mask, with a defect inspecting pattern, formed on a transparent substrate; preparing a mask defect inspecting apparatus that may include a defect inspecting unit that detects defects by radiating light on a surface of a mask and obtains an image based on the reflected light, and a mask stage on which the mask is mounted facing the defect inspecting unit; mounting the mask on the mask stage; and detecting mask defects by operating the defect inspecting unit to radiate light on a surface of the mask and obtain an image.

In an embodiment of the present invention, the method may include mounting a mask cassette storing the mask on a loading unit and attaching a mapping bar to the mask cassette to guide cassette mapping and enable the loading unit to recognize that the mask is stored in the cassette.

In an embodiment of the present invention, the mask defect inspecting apparatus may be prepared by replacing the wafer stage of a wafer defect inspecting apparatus with a mask stage, such that the mask stage supports a mask at a surface height substantially equal to a surface height of a wafer mounted on the wafer stage In an embodiment of the present invention, the method may include: mounting a mask cassette storing the mask on a loading unit on which a wafer storage cassette of the wafer defect inspecting apparatus is mounted; and attaching a mapping bar to the mask cassette to guide cassette mapping and enable the loading unit to recognize that the mask is stored in the cassette.

In an embodiment of the present invention, the mapping bar may be a transverse bar of a thickness substantially equal to a thickness of the wafer and installed rearward of where the mask is stored in the mask cassette, to enable the loading unit to recognize the stored mask as a wafer during cassette mapping of the loading unit.

In an embodiment of the present invention, the method may include replacing a wafer conveying robot arm of the wafer defect inspecting apparatus with a mask conveying robot arm, to convey the mask from the mask cassette to the mask stage.

In an embodiment of the present invention, the method may include reducing a height of a hub shaft supporting the mask stage by at least a difference between thicknesses of the wafer and the mask, to enable a surface height of the mask mounted on the mask stage to be substantially equal to a surface height of the wafer mounted on the wafer stage.

In an embodiment of the present invention, the method may include attaching a wafer-shaped wing with a notch corresponding to the notch of the wafer, on the mask stage, to pre-align the mask mounted on the mask stage.

In an embodiment of the present invention, the method may include test marks disposed on at least three positions of an outer region of a chip die region on the mask at mutually opposing directions, to enable the defect inspecting unit to recognize and map a position of the chip die region on the mask.

In an embodiment of the present invention, the mask may be prepared by: forming a mask layer on the transparent substrate; and forming the pattern through forming a resist layer on the mask layer and performing developing, wherein the defect inspecting is performed with an ADI (after development inspection).

In another embodiment of the present invention, an apparatus for mask defect inspection, may include: a wafer defect inspecting apparatus including a defect inspecting unit inspecting defects through radiating light on a surface of a wafer and obtaining an image from reflected light, and a wafer stage having the wafer mounted thereon facing the defect inspecting unit; a mask with a pattern for inspecting defects formed on a transparent substrate; and a mask stage installed to replace the wafer stage, to support the mask at a surface height equal to a surface height of the wafer installed on the wafer stage, wherein the defect inspecting unit is operated to radiate light on the surface of the mask and obtain an image, to detect mask defects.

In an embodiment of the present invention, the apparatus may include a mask cassette on a loading unit on which a wafer storage cassette of the wafer defect inspecting apparatus is mounted, the mask cassette being configured to store the mask and including a mapping bar attached thereon to enable recognizing and cassette mapping of a stored wafer.

In an embodiment of the present invention, the apparatus may include a mask conveying robot arm installed to replace a wafer conveying robot arm of the wafer defect inspecting apparatus, the mask conveying robot arm having a width greater than the wafer conveying robot arm, the mask conveying robot arm conveying the mask from the mask cassette to the mask stage.

In an embodiment of the present invention, the apparatus may include a hub shaft supporting the mask stage that is reduced by a difference in thicknesses of the wafer and the mask, to make a surface height of the mask mounted on the mask stage substantially equal to a surface height of the wafer mounted on the wafer stage.

In an embodiment of the present invention, the apparatus may include a wafer-shaped wing, with a notch corresponding to a notch of the wafer, to pre-align the mask mounted on the mask stage.

DESCRIPTION OF SPECIFIC EMBODIMENTS

Figure 1:
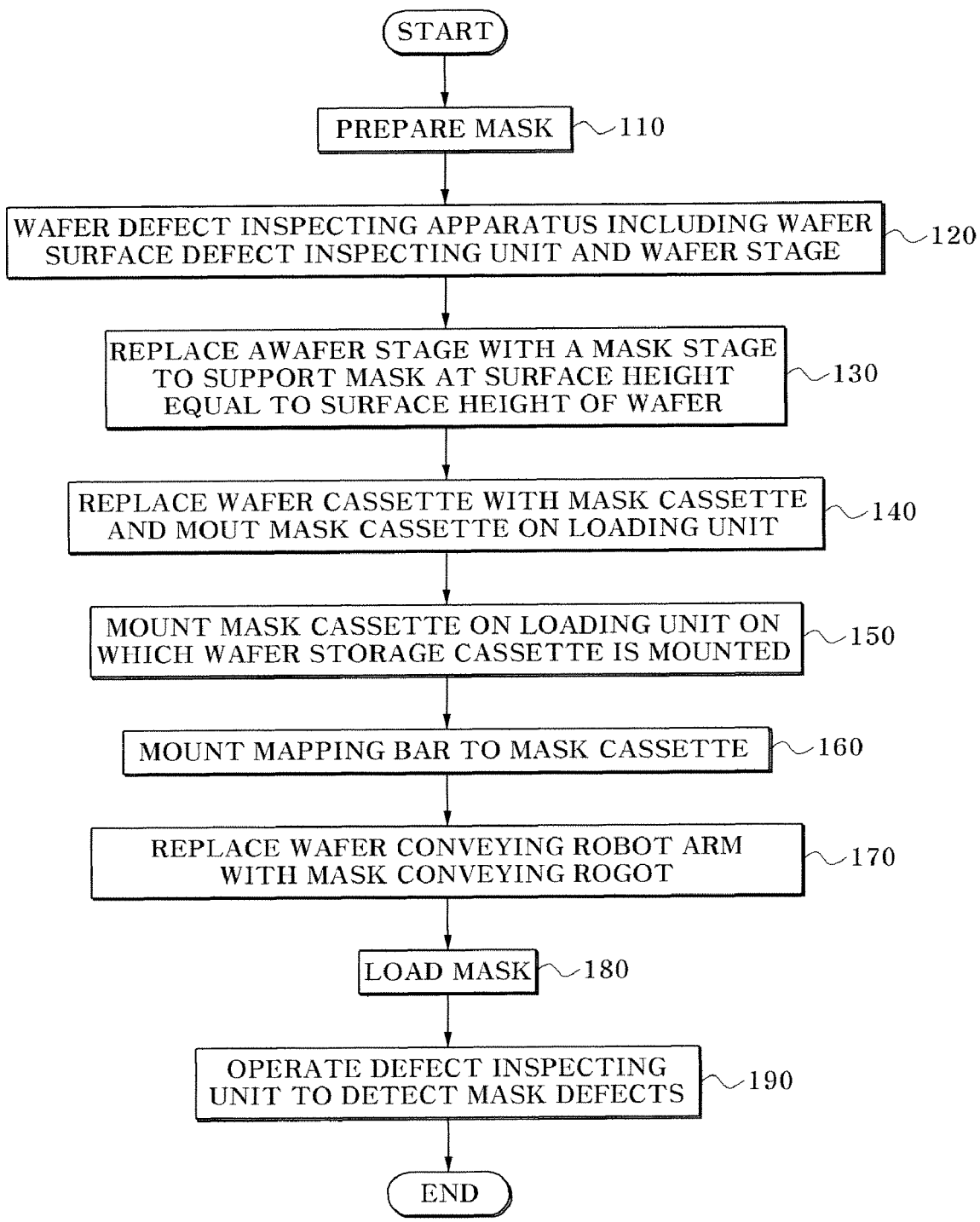
FIG. 1 illustrates a flowchart of a mask defect inspecting method according to an embodiment of the present invention.

A mask defect inspecting apparatus is used to conduct inspections of pattern defects on mask surfaces. A wafer defect inspecting apparatus may be used to inspect pattern defects on mask surfaces as well. For example, idle wafer defect inspecting apparatuses such as KLA-Tencor's KLA2135 model may be used to perform inspection of mask defects. When considering a reduction exposure process, a wafer pattern formed on a wafer has a finer line width than a mask pattern formed on a mask. Therefore, the wafer defect inspecting apparatus has a higher resolution than a current mask defect inspecting apparatus and may prove better able to detect fine mask pattern defects.

However, while a wafer defect inspecting apparatus is configured to be capable of performing defect inspection of a wafer, it is difficult for the apparatus to perform mask defect inspection by directly loading a mask. The thickness of a mask without a pellicle attached is approximately 6.3 mm, which is considerably greater than a wafer thickness of approximately 0.725 mm. Thus, it is difficult to load a mask directly on a wafer defect inspecting apparatus.

For example, in the case of a wafer defect inspecting apparatus, the distance set between the surface of a chuck-loaded wafer and an immersion lens of a defect inspecting unit is approximately 0.863 mm (34 mil). Thus, direct chuck loading of a mask is not possible. Because the settings are calibrated for a cassette loading unit or wafer cassette loading unit, when directly loading a mask cassette, the thickness discrepancy of a stored mask prevents performance of load mapping. Specifically, a mapping sensor for loading is set to recognize a wafer based on the thickness of a wafer, so that a mapping sensor cannot recognize a thicker mask. Moreover, a wafer conveyor robot arm is formed in the shape of a fork suitable for conveying wafers and is not suited to the geometry of a mask. When using a wafer conveyor robot arm to convey a mask there is the danger of the mask disengaging, falling, and being damaged. Furthermore, because a mask is a flat rectangular or square shape, whereas a wafer is round with a notch, when a mask is mounted on a chuck stage, it is not possible to pre-align it for defect inspection.

In accordance with embodiments of the herein described invention, a wafer defecting inspecting apparatus advantageously may be made compatible for mask defect inspection.

The setting of the gap for the inspection, based on a pellicle being attached to a mask, is revised to perform a defect inspection of a mask surface without a pellicle attached thereto. By not considering the attachment of a pellicle, the distance between the surface of the mask and the immersion lens of the defect inspecting unit can be reduced substantially to attain a higher NA. For example, the distance can be reduced by approximately 0.863 mm (34 mil). With a higher NA, the resolution of images can be improved, allowing for the detection of smaller-sized defects.

To further improve resolution of the images for detecting defects, light is radiated on the surface of the mask and images are produced based on the reflected light. By obtaining images based on reflected light, rather than based on light that passes through the mask, a higher NA can be derived, so that finer sized defects can be detected. Accordingly, improvements in mask manufacturing yield and consequent improvements in wafer manufacturing yield can be attained.

Figure 6:
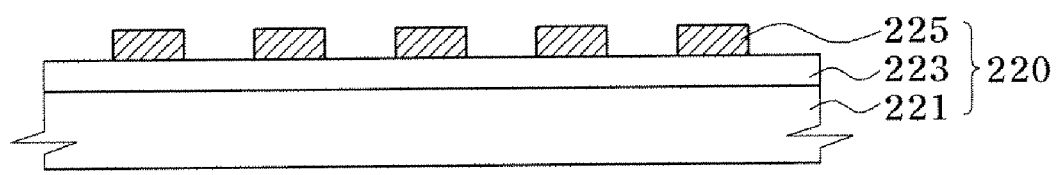
FIG. 6 illustrates a mask configuration on which a mask defect inspection may be performed, according to an embodiment of the present invention.

Referring to FIG. 1, a mask defect inspecting method may include preparing a mask, with a defect inspection pattern, on a transparent substrate 110. The mask, as illustrated in FIG. 6, may include a mask layer 223 with a chrome light shielding layer or a halftone phase shift layer on a transparent substrate 221, and a mask 220 that is electron beam write exposed and developed through a resist pattern 225 may be prepared on the mask layer 223. That is, right after developing, it may be prepared as the mask 220. Also, the mask layer 223 may be selectively etched according to the shape of the resist pattern 225 and prepared as a mask with a patterned structure. The attachment of the pellicle is eliminated for the sake of attaining a higher NA in the process of forming a surface pattern image for detecting defects. Thus, the mask 220 is prepared to directly inspect the formed surface of the pattern 225 for defects.

Referring again to FIG. 1, a wafer defect inspecting apparatus having a wafer chuck stage for a wafer surface defect inspecting unit and for mounting a wafer may be prepared 120. This wafer defect inspecting apparatus may be configured as a wafer pattern defect inspecting apparatus, and may be configured as an apparatus used during the manufacturing process of a wafer. The wafer defect inspecting apparatus may use a state, capable of being categorized as an idle apparatus according to the design rule of the semiconductor device. For example, an apparatus (such as KLA-Tencor's KLA2135 model) that is used for the manufacturing of semiconductor devices with larger wafer patterns, may be prepared.

A wafer defect inspecting apparatus with a higher resolution may be used to detect mask defects, or a mask defect inspecting apparatus having the same structure as the defect inspecting unit of an actual wafer defect inspecting apparatus may be designed to perform inspections of defects. By using conventional idle wafer defect inspecting apparatuses, equipment cost can be reduced and resources can be reused.

When considering size reduction and exposure, a mask pattern formed on a mask is substantially larger in size than an actual wafer pattern, so that even if defect inspecting units of past generation wafer defect inspecting apparatuses are used to perform inspecting of mask defects, finer defects can be detected.

Figure 2:
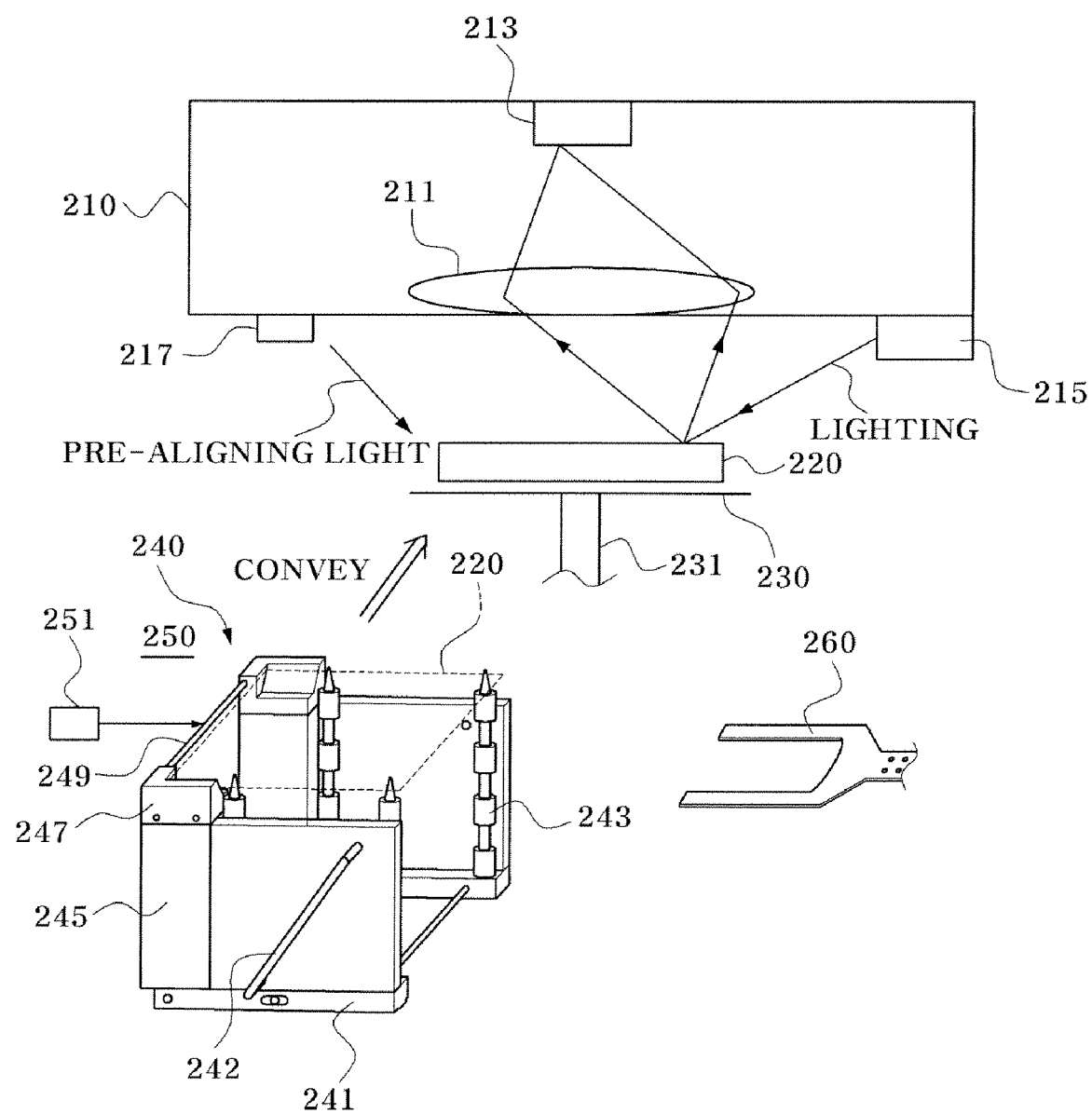
FIG. 2 illustrates a mask defect inspecting apparatus according to an embodiment of the present invention.

Referring to FIGS. 1 and 2, in order to accommodate the geometry of a mask, a chuck stage (or a wafer stage) installed opposite to a defect inspecting unit 210 of a wafer defect inspecting apparatus is replaced with a mask stage 230 (130 in FIG. 1). The mask stage 230 is installed to be able to load the mask 220.

The defect inspecting unit 210 may be configured to obtain a surface image of a region for defect inspection. For example, the defect inspecting unit 210 may be formed with an immersion lens unit 211 for obtaining an image and an immersion imaging device 213. A lighting unit 215 that radiates light on a surface of the mask 220 may be included. The radiated light may be reflected from the surface of the mask, provide an image incident on the immersion lens unit 211.

The defect inspecting unit 210 includes a pre-alignment inspecting unit 217 for pre-alignment of the mask 220 mounted on the mask stage 230. The lighting unit 215, immersion lens unit 211, and the pre-alignment inspecting unit 217 may be disposed and installed in a configuration that substantially corresponds to the configuration of these elements in a wafer defect inspecting apparatus.

The mask stage 230 is installed such that the distance between the mask 220 thereon and the immersion lens 211 is maintained substantially equal to the distance between the wafer and the immersion lens unit. In the case of model KLA2135, for example, the distance is approximately 0.863 mm (34 mil). In this case, to retain a distance between the mask 220 and an immersion lens unit 211 with a magnification of approximately 50×, the height of the mask stage 230 may be adjusted. In other words, when a wafer defect inspecting apparatus is used for mask defect inspection, the mask stage 230 may be installed to sustain the surface height of the mask 220 at substantially the same level as the surface height of a wafer mounted on a wafer stage.

The thickness of the mask 220 without the pellicle is approximately 6.3 mm, which is a value substantially greater than the thickness of the wafer that is approximately 0.725 mm. Thus, a mask stage 230 with a reduced thickness that is less than the wafer stage in a chuck stage format may be manufactured, or a hub shaft 231 supporting the mask stage 230 may be reduced in height so that the mask 220 may be mounted at substantially the same level as the surface height of a wafer mounted on a wafer stage.

Figure 3:
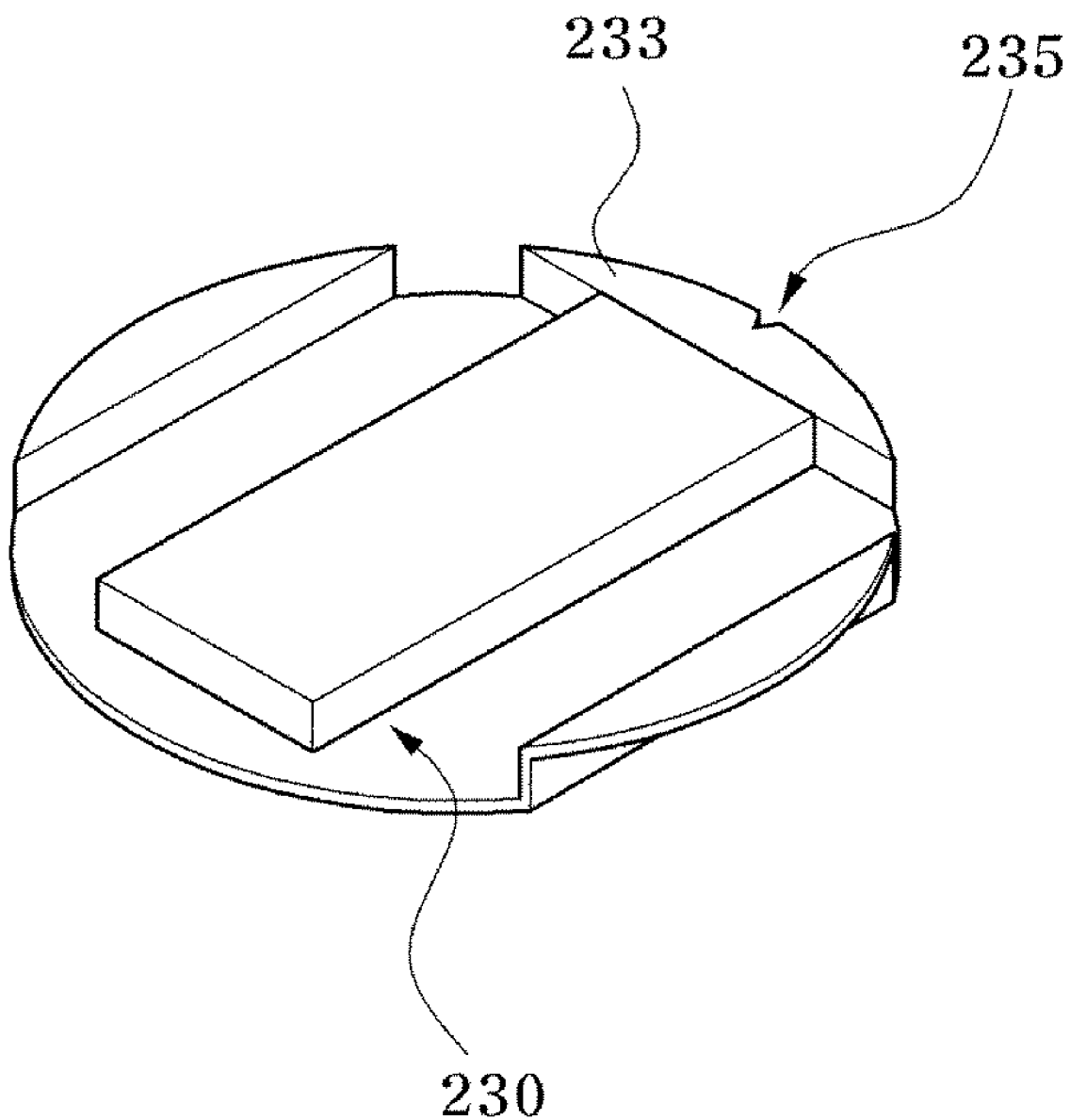
FIG. 3 illustrates a mask stage according to an embodiment of the present invention.

Also, as a result of the difference in geometry between a wafer and a mask, it is difficult to pre-align a mask 220 using the pre-alignment inspecting unit 217 of a wafer defect inspecting apparatus. When pre-alignment does not occur, the actual performing of a defect inspecting process is difficult. Referring to FIG. 3, a wafer-shaped wing 233 may be added to the mask stage 230 (FIG. 1 operation 140) to allow for pre-alignment of the mask stage 230 by the pre-alignment unit 217 of a wafer inspecting apparatus.

By attaching the wing 233, the planar shape of the overall mask stage 230 has a shape corresponding to the shape of the wafer. Also, an inspection guide notch 235 may be provided on the wing 233 to correspond to the notch of the wafer. The inspection guide notch 235 may be installed corresponding to the flat zone of the wafer. By inspecting the inspection guide notch 235 with the pre-alignment light, the pre-alignment inspecting unit 217 may treat the mask 220 as a wafer and perform a pre-alignment of the mask 220 mounted on the mask stage 230.

The wafer and the mask 220 are different, so that the configurations of a mask cassette 240 and a wafer cassette are different. When using a wafer defect inspecting apparatus, a mask cassette 240 instead of a wafer cassette may be loaded on the loading unit 250 (in FIG. 2) (FIG. 1 operation 150).

Loading and mounting a stored mask 220 using a mapping inspecting unit 251 of a wafer defect inspecting apparatus is difficult. The mapping inspecting unit 251 cannot recognize the mask 220 because of the differences in geometry between the mask 220 and the wafer. To prevent this, a guide mapping bar 249 may be installed to enable the mapping inspecting unit 251 of a wafer defect inspecting apparatus to recognize the mask 220 as a wafer.

Figure 4:
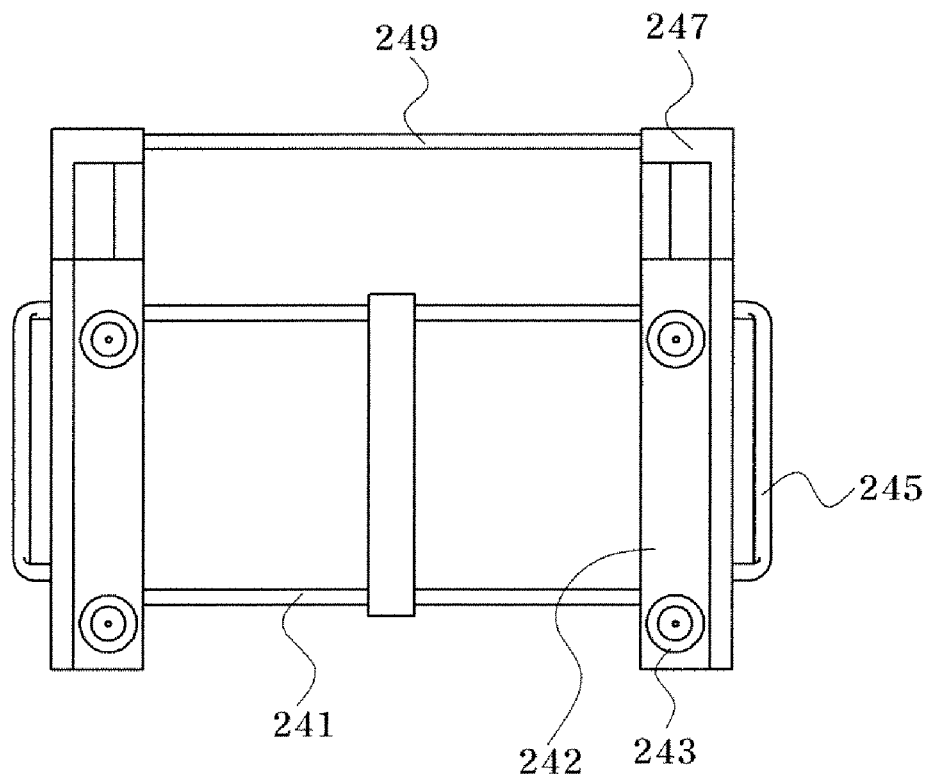
FIG. 4. illustrates a mask cassette according to an embodiment of the present invention.

Referring to FIG. 4, a guide mapping bar 249 may be installed behind the mask cassette 240 of the mapping inspecting unit 251. The guide mapping bar 249 may be installed corresponding to the fourteenth slot of a wafer cassette, to allow the mapping inspecting unit 251 to recognize that there is one wafer.

The guide mapping bar 249 may be a transverse bar that substantially corresponds in thickness and diameter with a wafer, so that when a mask 220 is stored, the mapping inspecting unit 251 will recognize the mask as a wafer. The mapping inspection may be conducted by emitting and collecting light. The mask cassette 240 may include four slit columns 243 on a floor 241 and two guides posts 245 for supporting a guide member 247 for guiding the upward conveyance of a mask 220 for storage. The guide member 247 may guide the mask 220 that is stored by having a sloped surface so that the mask 220 can be mounted by sliding. A handle 242 may be installed in opposition on the side surfaces. A guide mapping bar 249 may be installed between the guide members 247 on either side.

Figure 5:
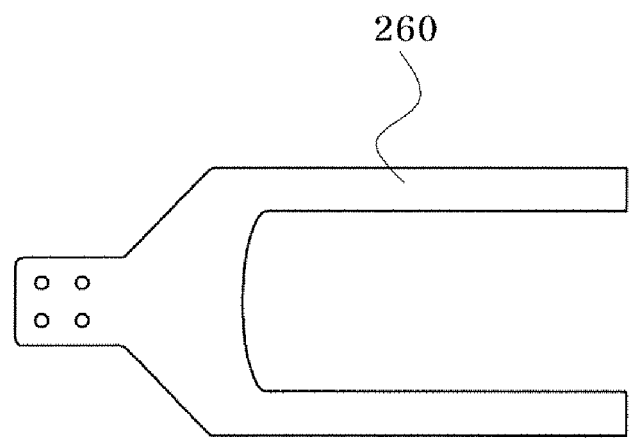
FIG. 5. illustrates a mask conveying robot arm according to an embodiment of the present invention.

To convey the mask 220 stored in the mask cassette 240 to the mask stage 230, a conveying robot arm 260 in FIG. 2 is configured as illustrated in FIG. 5 and installed in operation 170 of FIG. 1. The mask 220 is different in size and weight from a wafer, so that when a wafer conveying robot arm conveys the mask 220, the mask 220 is susceptible to disengagement and falling and damage. Referring to FIG. 5, to prevent damage to the mask, a fork type mask conveying robot arm 260 with a shape and size substantially corresponding to that of the mask. Therefore, safe handling of the mask 220 is possible.

Referring to FIGS. 1 and 6, the mask 220 (in FIG. 6) is loaded on the mask defect inspecting apparatus in FIG. 6 in operation 180 (FIG. 1), and the defect inspecting unit 210 (in FIG. 2) is operated to detect mask defects in operation 190 (FIG. 1). Referring to FIG. 2, the defect inspecting unit 210 radiates light on the surface of the mask 220 and collects the reflected light with the immersion lens 211, a surface image accompanying the collected light may obtained using a capturing device 213, and defects on the surface of the mask 220 may be detected based on the image.

Figure 7:
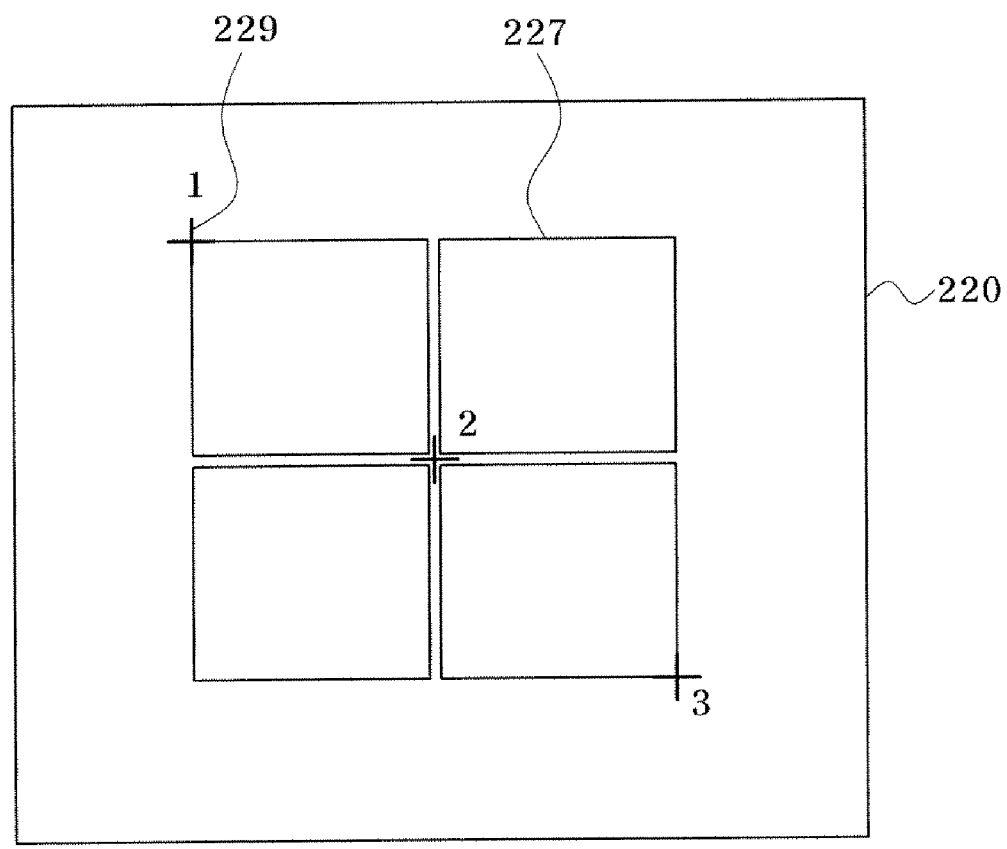
FIG. 7 illustrates a test mark configuration of a mask on which a mask defect inspection may be performed, according to a further embodiment of the present invention.

Referring to FIG. 7, the mask 220 may further include a test mark 229 disposed in a diagonal direction in an outer region of a chip die region 227 where a pattern is disposed (a scribe lane region, for example). The test mark 229 may perform the function of an aligning key and be disposed at least at three points. When the chip die region is in a 3×3 configuration, for example, alignment of the defect inspecting unit 210 for obtaining a surface image can be performed. In the case of a mask 220 where a chip die region 227 is in a 2×2 configuration, for example, (and not a 3×3 configuration), additional test marks 229 may be provided as additional aligning keys. Therefore, when using a wafer defect inspecting apparatus to inspect mask defects the defect inspecting unit 210 may be configured for an operation setting job or setting data as in the recognition of a wafer.

Referring to FIGS. 2 to 5, using a mask defect inspecting apparatus of the present invention to perform mask defect inspections results in a similar level of sensitivity as a conventional high-resolution mask defect inspecting apparatus. Also, the mask defect inspecting apparatus of the present invention may perform inspection in approximately one-third of the time it takes a conventional mask defect inspecting apparatus, which has an average inspection time of approximately 20 minutes. Additionally, by using reflected light to detect defects, it is possible to inspect a light blocking layer such as a chrome layer or a halftone phase shift layer that is not patterned, allowing, for example, inspection of a blank mask or after develop inspection (ADI). When performing ADI, the variation in the line thickness of the resist pattern before and after the inspection lies within a tolerance range and can therefore be ignored.

The sensitivity of the defect inspection, when using a programmed mask and a cell to cell method for a cell array and a random/die to die method, ranges from approximately 150 nm to approximately 450 nm. Moreover, in the case of an ArF light source halftone phase shift mask, defect inspection is possible for an approximately 80 nm mask even with a chrome layer retained, where the detection sensitivity is approximately 200 nm. In a KrF light source halftone mask with a chrome layer removed, defect inspection is possible for an approximately 100 nm mask, where the detection sensitivity is approximately 200 nm. These comparative results show that a higher detecting ability may be obtained when using the method and apparatus of the present invention.

A mask defect inspecting method and apparatus according to the present invention for inspecting finer masks has been described above. Also, inspection of a blank mask or ADI, that is not possible with inspecting methods relying on transmitted light, is possible with the method and apparatus provided herein. Furthermore, defect inspection of fine masks may be performed at a lower cost.

While the present invention has been described with respect to the specific embodiments, it will be apparent to those skilled in the art that various changes and modifications may be made without departing from the spirit and scope of the invention as defined in the following claims.

What is claimed is:

1. A method for inspecting mask defects, comprising:
   preparing a mask, with a pattern on a transparent substrate;
   preparing a mask defect inspecting apparatus comprising a defect inspecting unit, a loading unit and a mask stage;
   mounting a mask cassette, storing the mask, on the loading unit;
   attaching a mapping bar to the mask cassette to guide cassette mapping and to enable the loading unit to recognize that the mask is stored in the mask cassette;
   mounting the mask on the mask stage, such that the mask is facing the defect inspecting unit and is supported at a surface height such that the defect inspecting unit can operate by radiating light on a surface of the mask; and
   detecting mask defects by operating the defect inspecting unit to radiate light on the surface of the mask and obtain an image based on reflected light.

2. The method of claim 1 further comprising conveying the mask from the mask cassette to the mask stage with a mask conveying robot arm, wherein the mask conveying robot arm has a size and a shape that substantially corresponds to a size and a shape of the mask.

3. The method of claim 1, further comprising placing test marks disposed on at least three positions of an outer region of a chip die region on the mask at mutually opposing directions, to enable the defect inspecting unit to recognize and map a position of the chip die region on the mask.

4. A method for inspecting mask defects, comprising:
   preparing a mask, with a pattern formed on a transparent substrate;
   preparing a mask defect inspecting apparatus comprising a defect inspecting unit, a loading unit and a mask stage;
   replacing a wafer storage cassette with a mask cassette, storing the mask, and mounting the mask cassette on a loading unit;
   attaching a mapping bar to the mask cassette to guide cassette mapping and to enable the loading unit to recognize that the mask is stored in the mask cassette;
   mounting the mask on the mask stage; and
   detecting mask defects through operating the defect inspecting unit to radiate light on a surface of the mask and to obtain an image based on reflected light;
   wherein the mask defect inspecting apparatus is prepared by replacing a wafer stage of a wafer defect inspecting apparatus with the mask stage such that the mask is mounted on the mask stage at a surface height substantially equal to a surface height of a wafer mounted on the wafer stage.

5. The method of claim 4, wherein the mapping bar is a transverse bar having a thickness substantially equal to a thickness of the wafer and attached rearward of where the mask is stored in the mask cassette, to enable the loading unit to recognize the stored mask as the wafer during cassette mapping of the loading unit.

6. The method of claim 4, further comprising replacing a wafer conveying robot arm of the wafer defect inspecting apparatus with a mask conveying robot arm, wherein a size and a shape of the mask conveying robot arm substantially corresponds to a size and shape of the mask, to convey the mask from the mask cassette to the mask stage.

7. The method of claim 4, further comprising reducing a height of a hub shaft supporting the mask stage by at least a difference between thicknesses of the wafer and the mask, to enable a surface height of the mask mounted on the mask stage to be equal to a surface height of the wafer mounted on the wafer stage.

8. The method of claim 4, further comprising attaching a wafer-shaped wing, with a notch corresponding to the notch of the wafer, on the mask stage, to pre-align the mask mounted on the mask stage.

9. The method of claim 4, further comprising test marks disposed on at least three positions of an outer region of a chip die region on the mask at mutually opposing directions, to enable the defect inspecting unit to recognize and map a position of the chip die region on the mask.

10. The method of claim 4, wherein the preparing of the mask comprises:
    fowling a mask layer on the transparent substrate; and
    forming the pattern through forming a resist layer on the mask layer and performing developing, wherein the defect inspecting is performed with an ADI (after development inspection).

11. An apparatus for mask defect inspection, comprising:
    a mask, with a pattern, formed on a transparent substrate;

a defect inspecting unit inspecting defects by radiating light on a surface of the mask and obtaining an image from reflected light; and a mask stage having the mask mounted thereon facing the defect inspecting unit, wherein the mask stage supports the mask at a surface height that the defect inspecting unit is operated to radiate light on the surface of the mask and obtain an image to detect mask defects; and a mask cassette being configured to store the mask, wherein a mapping bar is attached to the mask cassette to enable recognizing and cassette mapping of the mask.

12. The apparatus of claim 11, further comprising a mask conveying robot arm having a size and a shape that substantially corresponds to a size and a shape of the mask, wherein the mask conveying robot arm conveys the mask from the mask cassette to the mask stage.

13. The apparatus of claim 11, wherein the mask stage further comprises a wafer-shaped wing with a notch corresponding to a notch of the wafer, to pre-align the mask mounted on the mask stage.

14. An apparatus for mask defect inspection, comprising:
a wafer defect inspecting apparatus comprising a defect inspecting unit and a mask stage;
a mask, with a pattern, formed on a transparent substrate; and
a mask cassette mounted on a loading unit of the wafer defect inspecting apparatus, wherein the mask cassette is installed to replace a wafer storage cassette, wherein the mask cassette is configured to store the mask and comprises a mapping bar attached to the mask cassette to enable recognizing and cassette mapping of a stored mask;

wherein the mask stage is installed to replace a wafer stage, and the mask stage supports the mask at a surface height substantially equal to a surface height of a wafer installed on the wafer stage;

wherein the defect inspecting unit is operated to radiate light on the surface of the mask and obtain an image to detect mask defects.

15. The apparatus of claim 14, further comprising a mask conveying robot arm installed to replace a wafer conveying robot arm of the wafer defect inspecting apparatus, the mask conveying robot arm having a size and a shape that substantially corresponds to a size and a shape of the mask, wherein the mask conveying robot arm conveys the mask from the mask cassette to the mask stage.

16. The apparatus of claim 14, further comprising a hub shaft supporting the mask stage that is reduced by a difference in thicknesses of the wafer and the mask, to make a surface height of the mask mounted on the mask stage substantially equal to a surface height of the wafer mounted on the wafer stage.

17. The apparatus of claim 14, wherein the mask stage further comprises a wafer-shaped wing, with a notch corresponding to a notch of the wafer, to pre-align the mask mounted on the mask stage.

* * * * *

UNITED STATES PATENT AND TRADEMARK OFFICE
CERTIFICATE OF CORRECTION

PATENT NO. : 7,764,368 B2
APPLICATION NO. : 11/965197
DATED : July 27, 2010
INVENTOR(S) : Sung H. Oh et al.

Page 1 of 1

It is certified that error appears in the above-identified patent and that said Letters Patent is hereby corrected as shown below:

In the Claims:

At Column 8, line 61, "fowling" should be -- forming --.

Signed and Sealed this
Eleventh Day of January, 2011

David J. Kappos
*Director of the United States Patent and Trademark Office*